United States Patent [19]
Bacskai

[11] Patent Number: 4,843,175
[45] Date of Patent: Jun. 27, 1989

[54] PROCESS FOR THE PREPARATION OF ALKYLANILINE USING A FRIEDEL-CRAFTS CATALYST

[75] Inventor: Robert Bacskai, Kensington, Calif.

[73] Assignee: Chevron Research Company, San Francisco, Calif.

[21] Appl. No.: 925,198

[22] Filed: Oct. 31, 1986

[51] Int. Cl.$^4$ .............................................. C07C 85/24
[52] U.S. Cl. ..................................... 564/409; 564/408
[58] Field of Search ................................ 564/408, 409

[56] References Cited

U.S. PATENT DOCUMENTS

| 3,649,693 | 3/1972 | Napolitano | 564/404 |
| 3,654,331 | 4/1972 | Klopfer | 564/408 |
| 3,843,698 | 10/1974 | Dunn | 564/409 |
| 3,941,844 | 3/1976 | Szymanski et al. | 564/408 |
| 4,739,121 | 4/1988 | Shaw | 564/409 |

OTHER PUBLICATIONS

Kirk–Othmer, *Encyclopedia of Chemical Technology,* 2nd Ed., vol. 10, pp. 135–141 & 158–163.

Primary Examiner—Richard L. Raymond
Attorney, Agent, or Firm—S. R. La Paglia; R. C. Gaffney; C. J. Caroli

[57] ABSTRACT

A process for the preparation of alkylaniline having from about 10 to 30 carbon atoms in the alkyl substituent which comprises reacting aniline with an olefin having from about 10 to 30 carbon atoms in the presence of a Friedel-Crafts catalyst.

8 Claims, No Drawings

PROCESS FOR THE PREPARATION OF ALKYLANILINE USING A FRIEDEL-CRAFTS CATALYST

BACKGROUND OF THE INVENTION

The present invention relates to a process for the preparation of an alkylaniline having about 10 to 30 carbon atoms in the alkyl substituent which comprises reacting aniline with an olefin in the presence of a Friedel-Crafts catalyst.

It is known in the art that aromatic amines, such as aniline, may be alkylated with olefins in the presence of aluminum or aluminum-containing catalysts. In general, the olefins employed to alkylate the aromatic amine are lower molecular weight olefins, such as ethylene, propylene and butylene.

Thus, U.S. Pat. No. 3,275,690 discloses the alkylation of an aromatic amine, such as aniline, with a lower aliphatic olefin or cyclo-olefin in the presence of a Friedel-Crafts catalyst or a mixture of a Friedel-Crafts catalyst and aluminum or an alkali or alkaline earth metal. This patent teaches the use of lower aliphatic olefins having up to 5 carbon atoms and states that the olefins of interest are the normally gaseous olefins, such as ethylene, propylene, butylene-1, butylene-2 and isobutylene. This patent further teaches that cyclohexene is a suitable cyclo-olefin, but that olefins such as styrene are not contemplated for use in the process therein.

British Pat. No. 823,223 discloses a process for the production of alkylated aromatic amines by the reaction of an aromatic amine with an aliphatic olefin having up to 4 carbon atoms. The reaction is catalyzed by a number of aluminum-containing catalyst mixtures, such as a mixture of aluminum or an alloy of aluminum with a Friedel-Crafts catalyst.

U.S. Pat. No. 2,762,845 discloses a process for the production of nuclearly alkylated aromatic amines by the reaction of an aromatic amine with an olefin in the presence of aluminum. The aluminum can be added as metallic aluminum or as an aluminum alloy. Olefins which are described in this patent as suitable include ethylene, propylene, butylene, isobutylene, cyclohexene and styrene.

U.S. Pat. No. 2,814,646 discloses a process for the nuclear alkylation of a primary or secondary aromatic amine which comprises heating the amine with an olefin in the presence of an aluminum anilide catalyst. In this process, lower molecular weight olefins are preferred, such as ethylene, propylene and butylene.

U.S. Pat. No. 3,649,693 discloses a process for the selective orthoalkylation of aromatic amines which comprises heating an aromatic amine with an olefin in the presence of an aluminum anilide catalyst to form a reaction mixture containing orthoalkylated aromatic amines, and subsequently distilling the orthoalkylated aromatic amines from the reaction mixture without hydrolysis.

U.S. Pat. No. 3,923,892 discloses a process for the selective orthoalkylation of an aromatic amine which comprises reacting the aromatic amine with an olefin in the presence of an aluminum anilide catalyst, wherein the aluminum anilide catalyst is formed by adding an alkyl aluminum halide to the aromatic amine.

SUMMARY OF THE INVENTION

The present invention provides a process for the preparation of alkylaniline having from about 10 to 30 carbon atoms in the alkyl substituent which comprises reacting aniline with an olefin having from about 10 to 30 carbon atoms in the presence of a Friedel-Crafts catalyst.

Among other factors, the present invention is based on the surprising discovery that relatively long chain alkylanilines can be conveniently prepared in good yields by the reaction of aniline with higher molecular weight olefins having about 10 to 30 carbon atoms in the presence of a Friedel-Crafts catalyst.

DETAILED DESCRIPTION OF THE INVENTION

The process of the present invention will generally employ an olefin containing from about 10 to 30 carbon atoms. Olefins which are suitable for reaction with aniline may be either straight chain, slightly branched or highly branched in structure. These olefins are normally obtained by conventional procedures known to the art. For example, straight chain olefins may be conveniently obtained by the cracking of wax or from the ethylene growth reaction. Branched chain olefins may be readily prepared by the polymerization of lower molecular weight olefins, such as propylene or isobutylene. Preferred olefins for reaction with aniline are those which contain about 12 to 24 carbon atoms. Examples of preferred olefins include 1-dodecene and a $(C_{20-24})$-alpha olefin.

According to the process of the invention, the reaction of aniline with an olefin is carried out in the presence of a Friedel-Crafts catalyst. Suitable Friedel-Crafts catalysts include aluminum chloride, boron trifluoride, boron trifluoride-etherate, boron trichloride, aluminum bromide, and the like. Preferably, the Friedel-Crafts catalyst employed will be aluminum chloride or boron trifluoride-etherate. An especially preferred catalyst is aluminum chloride. The amount of catalyst utilized will generally range from about 0.1 weight percent to about 10 weight percent.

The molar ratio of olefin to aniline will normally range from about 10:1 to 1:10, and preferably will range from about 4:1 to 1:4.

The Friedel-Crafts catalyzed reaction of aniline with an olefin will generally take place in a pressure reactor at a pressure in the range of about 40 psi to 500 psi, preferably in the range of about 50 psi to 300 psi. The reaction temperature will generally range from about 150° C. to about 350° C., preferably from about 200° C. to about 300° C. The reaction will normally proceed over a period of about 0.5 to 8 hours. The resulting alkylamine is then separated from the catalyst residue and unreacted starting material, using conventional techniques.

The alkylaniline produced by the process of the present invention will generally contain a mixture of isomers, including ortho-, para-, and N-substituted alkylaniline. In general, the ortho-substituted alkylaniline will be the predominant isomer produced.

The alkyl side chain on the alkylaniline will normally contain from about 10 to 30 carbon atoms, and preferably will contain from about 12 to 24 carbon atoms. Examples of preferred alkylanilines produced by the present process include dodecylaniline and $(C_{20-24})$-alkylaniline The alkylanilines prepared by the process of the invention have utility as intermediates for the preparation of oligomeric amines which are useful as corrosion inhibitors, as described in commonly assigned copending U.S patent application Ser. No. 926,036, filed concurrently herewith, entitled "Alkylaniline/Formaldehyde Oligomers as Corrosion Inhibitors", now U.S. Pat. No. 4,780,278, and commonly assigned copending U.S. patent application Ser. No. 926,048, filed concurrently herewith, entitled "Alkylaniline/-Formaldehyde Co-oligomers as Corrosion Inhibitors", now U.S. Pat. No. 4,778,654.

The following examples are provided to illustrate the invention in accordance with the principles of this invention but are not to be construed as limiting the invention in any way except as indicated by the appended claims.

EXAMPLES

EXAMPLE 1 preparation of Dodecylaniline from Aniline and 1-Dodecene

A one-liter stainless steel autoclave was charged with 333 g (3.57 M) aniline, 169 g (1.0 M) 1-dodecene and 16.7 g anhydrous aluminum chloride. The autoclave was purged with nitrogen, then heated under nitrogen pressure (about 150 psi) at 250° C. and stirred for 3 hours. After cooling to room temperature, the reaction mixture was dissolved in 300 ml toluene, washed with 600 ml of 5% NaOH and twice with 600 ml water. Gas chromatographic analysis showed that the toluene solution contained 183.6 g (0.703 M) dodecylaniline and 26.3 g (0.156 M) dodecene. The toluene was evaporated and the residue was distilled under vacuum. The fraction boiling at 181° C./0.7 mm Hg was determined to be 99.1% dodecylaniline by gas chromatography.

Nitrogen analysis of the above distillate showed 5.41% nitrogen (theory=5.36%). Infrared analysis showed a strong absorption of 3400 and 3480 cm$^{-1}$, indicative of —$NH_2$ groups. $^{13}$C-NMR analysis showed the presence of 63% ortho-dodecylaniline, 7% para-dodecylaniline and 30% N-dodecylaniline.

EXAMPLE 2

Preparation of ($C_{20-24}$)-Alkylaniline

A one-liter stainless steel autoclave was charged with 350 g (3.76 M) aniline, 304 g (1.04 M) of a ($C_{20-24}$)-alpha-olefin obtained by the ethylene growth reaction, and 17.5 g anhydrous aluminum chloride. The autoclave was purged with nitrogen, then heated under nitrogen pressure (about 200 psi) at 250° C. and stirred for 3 hours. After cooling to room temperature, the reaction mixture was dissolved in 500 ml toluene, washed with 700 ml of 5% NaOH and then with 700 ml water. Gas chromatographic analysis showed that the toluene solution contained 226.2 g (0.584 M) of ($C_{20-24}$)-alkylaniline and 63 g (0.214 M) of ($C_{20-24}$)-alpha-olefin. The toluene was evaporated and the residue was distilled under vacuum. The fraction boiling at 233–258° C./0.5 mm Hg was determined to be 98.8% ($C_{20-24}$)-alkylaniline by gas chromatography.

Nitrogen analysis of the above distillate showed 3.55% nitrogen (theory=3.62%). Infrared analysis showed a strong absorption at 3400 and 3460 cm$^{-1}$,indicative of —$NH_2$ groups. $^{13}$C-NMR analysis showed the presence of 67% ortho-substituted ($C_{20-24}$)-alkylaniline, 10% parasubstituted ($C_{20-24}$)-alkylaniline and 23% N-substituted ($C_{20-24}$)-alkylaniline.

EXAMPLES 3–6

Preparation of Dodecylaniline from Aniline and 1-Dodecene Using Various Friedel-Crafts Catalysts A 16 ml stainless steel shaker type microreactor was charged under nitrogen with 7.0 g (0.075 M) aniline, 3.5 g (0.021 M) 1-dodecene and 0.35 g of a Friedel-Crafts catalyst as indicated in Table I. The molar ratio of aniline to 1-dodecene was 3.6:1. The reaction mixture was shaken at 250° C. for 4 hours. After cooling to room temperature, the reaction mixture was diluted with 20 ml toluene containing a 1-tetradecene internal standard. Following washing with 20 ml of 5% NaOH, the toluene solution was analyzed by gas chromatography. The results are summarized in Table I.

TABLE I

| | Preparation of Dodecylaniline by the Alkylation of Aniline with 1-Dodecene Using Various Friedel-Crafts Catalysts | | |
|---|---|---|---|
| Ex. No. | Catalyst | Conversion, %$^a$ | Selectivity to Alkylaniline, % |
| 3 | $AlCl_3$ | 84 | 91 |
| 4 | $AlBr_3$ | 62$^b$ | 91 |
| 5 | $BCl_3$ | 45 | 60 |
| 6 | $BF_3$-etherate | 49 | 91 |
| 7 | Al + $AlCl_3$ | 16 | 100 |

$^a$Based on 1-dodecene.
$^b$After 2 hours at 250° C.

EXAMPLE 7

The procedure of Examples 3–6 was followed, except that the catalyst used was a mixture of 0.2 g aluminu and 0.35 g aluminum chloride. The results are shown in Table I. As noted above, U.S. Pat. No. 3,275,690 discloses the alkylation of an aromatic amine with a lower aliphatic olefin in the presence of a Friedel-Crafts catalyst. This patent teaches that aluminum facilitates the alkylation with Friedel-Crafts catalysts, resulting in higher conversions.

By comparison, Table I shows that in alkylations with 1-dodecene, a catalyst mixture of aluminum and aluminum chloride provides a much poorer conversion than aluminum chloride alone (16% vs. 84%). These results demonstrate that higher olefins behave differently in the presence of Friedel-Crafts catalysts than the lower olefins taught in the prior art.

What is claimed is:

1. A process for the preparation of alkylaniline having from about 10 to 30 carbon atoms in the alkyl substituent which comprises reacting aniline with an olefin having from about 10 to 30 carbon atoms in the presence of a Friedel-Crafts catalyst selected from the group consisting of aluminum chloride, aluminum bromide, boron trichloride, boron trifluoride and boron trifluoride-etherate, and wherein the reaction is carried out in the absence of an aluminum anilide or a gallium anilide.

2. The process according to claim 1, wherein the olefin has from about 12 to 24 carbon atoms.

3. The process according to claim 2, wherein the olefin is 1-odecene.

4. The process according to claim 2, wherein the olefin is a ($C_{20-24}$)-alpha-olefin.

5. The process according to claim 1, wherein the Friedel-Crafts catalyst is aluminum chloride.

6. The process according to claim 1, wherein the molar ratio of olefin to aniline is about 10:1 to 1:10.

7. The process according to claim 1, wherein the reaction is carried out at a temperature of about 150° C. to 350° C.

8. The process according to claim 1, wherein the reaction is carried out at a pressure of about 40 psi to 500 psi.

* * * * *